(12) United States Patent
Giri et al.

(10) Patent No.: US 11,090,068 B2
(45) Date of Patent: Aug. 17, 2021

(54) VERTEBRAL BODY REAMING METHOD

(71) Applicant: CTL Medical Corporation, Addison, TX (US)

(72) Inventors: Bala K Giri, Dallas, TX (US); Jon Suh, Ambler, PA (US); Sean Suh, Milltown, NJ (US)

(73) Assignee: CTL Medical Corporation, Addison, TX (US)

( * ) Notice: Subject to any disclaimer, the term of this patent is extended or adjusted under 35 U.S.C. 154(b) by 81 days.

(21) Appl. No.: 16/678,889

(22) Filed: Nov. 8, 2019

(65) Prior Publication Data

US 2020/0146697 A1   May 14, 2020

Related U.S. Application Data

(60) Provisional application No. 62/757,575, filed on Nov. 8, 2018.

(51) Int. Cl.
*A61B 17/17* (2006.01)
*A61B 17/16* (2006.01)

(52) U.S. Cl.
CPC .. *A61B 17/1757* (2013.01); *A61B 2017/1602* (2013.01)

(58) Field of Classification Search
CPC ............... A61B 17/1757; A61B 17/1671
See application file for complete search history.

(56) References Cited

U.S. PATENT DOCUMENTS

| | | | |
|---|---|---|---|
| 2001/0000532 A1* | 4/2001 | Michelson | A61B 17/1757 606/80 |
| 2003/0191474 A1* | 10/2003 | Cragg | A61B 17/1757 606/79 |
| 2008/0015694 A1* | 1/2008 | Tribus | A61F 2/4611 623/17.11 |
| 2009/0182341 A1* | 7/2009 | Link | A61B 17/1757 606/99 |
| 2010/0016968 A1* | 1/2010 | Moore | A61B 17/15 623/17.11 |
| 2012/0136392 A1* | 5/2012 | Keegan | A61B 17/7059 606/249 |
| 2012/0271312 A1* | 10/2012 | Jansen | A61F 2/4611 606/80 |
| 2014/0018816 A1* | 1/2014 | Fenn | A61B 17/8875 606/104 |
| 2017/0340358 A1* | 11/2017 | Bullard | A61B 17/1757 |
| 2019/0142438 A1* | 5/2019 | Skajster | A61B 17/1671 606/79 |

* cited by examiner

*Primary Examiner* — Christian A Sevilla
(74) *Attorney, Agent, or Firm* — Brainspark Associates, LLC

(57) ABSTRACT

Disclosed are improved orthopedic tools and methods for use during orthopedic surgical procedures, including joint arthroplasty and joint replacement procedures. More specifically, disclosed herein are improved apparatus for preparing bone and/or soft tissue of the spine and/or other regions for implantation of intervertebral implants.

20 Claims, 10 Drawing Sheets

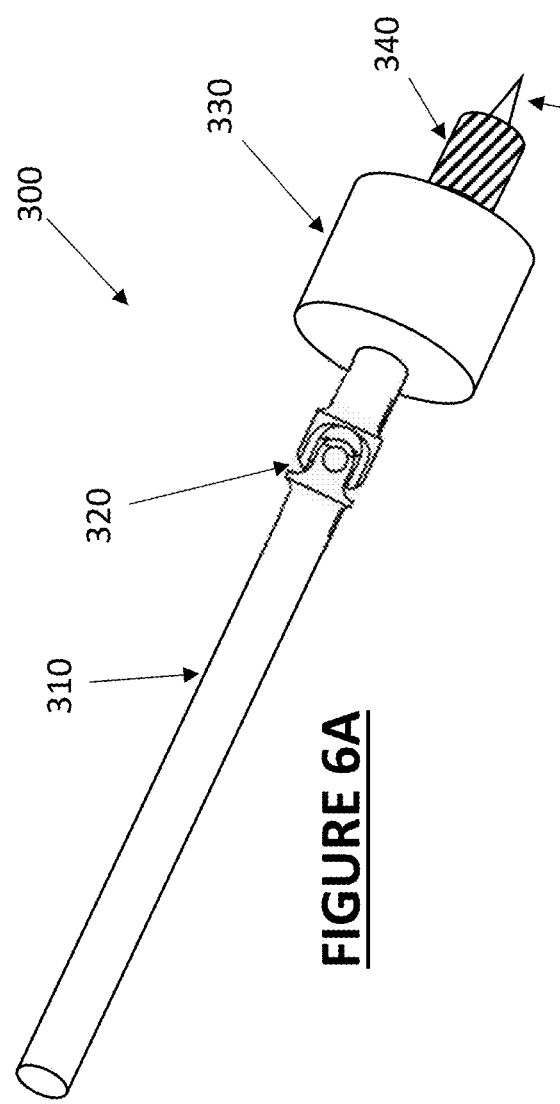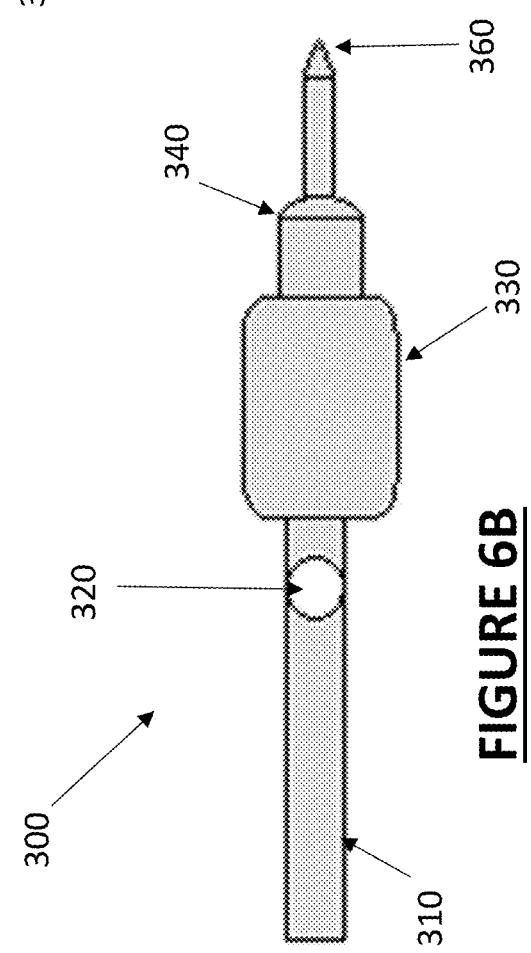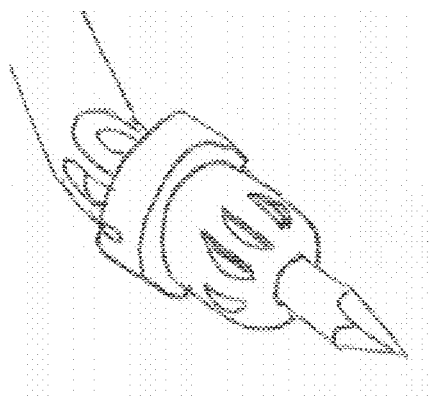

VERTEBRAL BODY REAMING METHOD

CROSS-REFERENCE TO RELATED APPLICATIONS

This application claims the benefit of U.S. Provisional Patent Application Ser. No. 62/757,575 entitled "MULTI-LEVEL PLATE-CAGE CONSTRUCTS AND METHODS," filed Nov. 8, 2018, the disclosure of which is incorporated by reference herein in its entirety.

TECHNICAL FIELD

The invention relates to improved orthopedic tools and methods for use during orthopedic surgical procedures, including joint arthroplasty and joint replacement procedures. More specifically, disclosed herein are improved apparatus for preparing bone and/or soft tissue of the spine and/or other regions for implantation of intervertebral implants.

BACKGROUND OF THE INVENTION

In mammals, the spinal (or vertebral) column is one of the most important parts of the body's support structure. The spinal column provides the main support necessary for mammals to stand, bend, and twist. In humans, the spinal column is generally formed by individual interlocking vertebrae, which are classified into five segments, including (from head to tail) a cervical segment (vertebrae C1-C7), a thoracic segment (vertebrae T1-T12), a lumbar segment (vertebrae L1-L5), a sacrum segment (vertebrae S1-S5), and coccyx segment (vertebrate Co1-Co5). The cervical segment forms the neck, supports the head and neck, and allows for nodding, shaking and other movements of the head. The thoracic segment attaches to ribs to form the ribcage. The lumbar segment carries most of the weight of the upper body and provides a stable center of gravity during movement. The sacrum and coccyx make up the back walls of the pelvis.

Intervertebral discs are located between each of the movable vertebra. Each intervertebral disc typically includes a thick outer layer called the disc annulus, which includes a crisscrossing fibrous structure, and a disc nucleus, which is a soft gel-like structure located at the center of the disc. The intervertebral discs function to absorb force and allow for pivotal movement of adjacent vertebra with respect to each other.

In the vertebral column, the vertebrae increase in size as they progress from the cervical segment to the sacrum segment, becoming smaller in the coccyx. At maturity, the five sacral vertebrae typically fuse into one large bone, the sacrum, with no intervertebral discs. The last three to five coccygeal vertebrae (typically four) form the coccyx (or tailbone). Like the sacrum, the coccyx does not have any intervertebral discs.

Each vertebra is an irregular bone that varies in size according to its placement in the spinal column, spinal loading, posture and pathology. While the basic configuration of vertebrae varies, every vertebra has a body that consists of a large anterior middle portion called the centrum and a posterior vertebral arch called the neural arch. The upper and lower surfaces of the vertebra body give attachment to intervertebral discs. The posterior part of a vertebra forms a vertebral arch that typically consists of two pedicles, two laminae, and seven processes. The laminae give attachment to the ligament flava, and the pedicles have a shape that forms vertebral notches to form the intervertebral foramina when the vertebrae articulate. The foramina are the entry and exit passageways for spinal nerves. The body of the vertebra and the vertical arch form the vertebral foramen, which is a large, central opening that accommodates the spinal canal that encloses and protects the spinal cord.

The body of each vertebra is composed of cancellous bone that is covered by a thin coating of cortical bone. The cancellous bone is a spongy type of osseous tissue, and the cortical bone is a hard and dense type of osseous tissue. The vertebral arch and processes have thicker coverings of cortical bone.

The upper and lower surfaces of the vertebra body are flattened and rough. These surfaces are the vertebral endplates that are in direct contact with the intervertebral discs. The endplates are formed from a thickened layer of cancellous bone, with the top layer being denser. The endplates contain adjacent discs and evenly spread applied loads. The endplates also provide anchorage for the collagen fibers of the disc. Each disc forms a fibrocartilaginous joint between adjacent vertebrae so as to allow relative movement between adjacent vertebrae. Beyond enabling relative motion between adjacent vertebrae, each disc acts as a shock absorber for the spinal column.

Each disc comprises a fibrous exterior surrounding an inner gel-like center which cooperate to distribute pressure evenly across each disc, thereby preventing the development of stress concentrations that might otherwise damage and/or impair vertebrae of the spinal column. Discs are, however, subject to various injuries and/or disorders which may interfere with a disc's ability to adequately distribute pressure and protect vertebrae. For example, disc herniation, degeneration, and infection of discs may result in insufficient disc thickness and/or support to absorb and/or distribute forces imparted to the spinal column. Disc degeneration, for example, may result when the inner gel-like center begins to dehydrate, which may result in a degenerated disc having decreased thickness. This decreased thickness may limit the ability of degenerated disc to absorb shock which, if left untreated, may result in pain and/or vertebral injury.

While pain medication, physical therapy, and other non-operative conditions may alleviate some symptoms, such interventions may not be sufficient for every patient. Accordingly, various procedures have been developed to surgically improve patient quality of life via abatement of pain and/or discomfort. Such procedures may include, discectomy and fusion procedures, such as, for example, anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF). During a discectomy, all or a portion of a damaged disc is removed via an incision, typically under X-ray guidance.

Following the discectomy procedure, a medical professional may determine an appropriate size of an interbody device or other spinal implant via one or more distractors and/or trials of various sizes. Each trial and/or distractor may be forcibly inserted between adjacent vertebrae. Upon determination of an appropriate size, one or more of an ACIF, ALIF, DLIF, PLIF, and/or TLIF surgical procedure may be performed by placing an appropriate interbody device (such as, for example, a cage, a spacer, a block) between adjacent vertebrae in the space formed by the removed degenerated disc. Placement of such interbody devices within the spinal column may prevent spaces between adjacent vertebrae from collapsing, thereby preventing adjacent vertebrae from resting immediately on top of one another and inducing fracture of the vertebra, impingement of the spinal cord, and/or pain. Additionally, such interbody devices may facilitate fusion between adjacent vertebrae by stabilizing adjacent vertebrae relative to one another. Accordingly, such interbody devices often may include one or more bone screws extending through the interbody device and into adjacent vertebrae.

Often, following the removal of a distractor and/or trial implant, a medical professional must prepare one or more bores or holes in a vertebra intended to receive the bone screws. Such holes may be formed with the aid of a separate drill guide positioned proximate or abutting vertebra and inserting a drill therethrough. Alternatively, such holes may be formed free hand, without the use of a drill guide. Further, since the spinal column is subject to dynamic forces, often changing with each slight movement of the patient, such screw(s) may have a tendency to back out (for example, unscrew) and/or dislodge from the interbody device, thereby limiting an interbody device's ability to stabilize adjacent vertebrae, and consequently, promote fusion. Additionally, if the screw(s) back out and/or dislodge from the interbody device, they may inadvertently contact, damage, and/or irritate surrounding tissue. Further, the interbody device is commonly comprised of a radiopaque material so as to be visible in situ via x-ray and other similar imaging modalities. However, such materials may impede sagittal and/or coronal visibility, thereby preventing visual confirmation of placement and post-operative fusion.

Thus, there remains a need for improved interbody devices, associated systems and surgical tools, and methodologies related thereto.

BRIEF SUMMARY OF THE INVENTION

The present disclosure includes examples that relate to, among other things, intradiscal, extradiscal, or interdiscal implants and related surgical tools. The surgical devices disclosed herein, and the cages, plating devices, and cage systems utilized therewith may be used as, for example, but not limited to, standalone anterior lumbar interbody fusion devices, standalone anterior low-profile plating devices, an interlocking of standalone devices to create hybrid devices, modular systems to allow interchangeability, and the like. Each of the examples disclosed herein may include one or more features described in connection with any of the other disclosed examples According to various non-limiting aspects of the disclosure, the disclosed surgical tools may have particular utility in conjunction with a cage for implanting in bone, said cage comprising: a first plate having a surface that contacts a first bone surface; a second plate having a surface that contacts a second bone surface; an intermediary plate that dynamically couples to the first plate and the second plate; an actuator that drives and causes the intermediary plate to move between the first plate and the second plate along a predetermined direction; and an anchor that attaches to the first plate and the second plate to engage the actuator to drive the actuator longitudinally along the predetermined direction. The cage may further comprise a pin that engages an anterior portion of the intermediary plate. The pin may engage a portion of the actuator to substantially affix the actuator to the intermediary plate. At least one of the first plate and second plate may comprise a guide track that engages and guides the intermediary plate as it moves between the first plate and the second plate along the predetermined direction. The intermediary plate may comprise a guide that engages the guide track to go guide the intermediary plate as it moves between and along inner surfaces of the first plate and the second plate in the predetermined direction. The anchor may comprise an anchor lock that engages the first plate or the second plate to prevent the anchor from moving, which, otherwise, may comprise rotation of the anchor about a longitudinal axis of the actuator. At least one of the first plate and the second plate may comprise a receiver that holds the anchor lock. The inner walls of the first plate, second plate and intermediary plate may form one or more graft chambers According to a still further aspect of the disclosure, surgical devices for preparing anatomical surfaces for implantation of a cage in bone comprises are disclosed herein.

BRIEF DESCRIPTION OF THE SEVERAL VIEWS OF THE DRAWINGS

FIG. 6A depicts a perspective view of one exemplary embodiment of a multi-axial reamer;

FIG. 6B depicts a side view of the multi-axial reamer of FIG. 6A; and

FIG. 6C depicts a partial view of a reamer head.

DETAILED DESCRIPTION OF THE INVENTION

Figure 1:
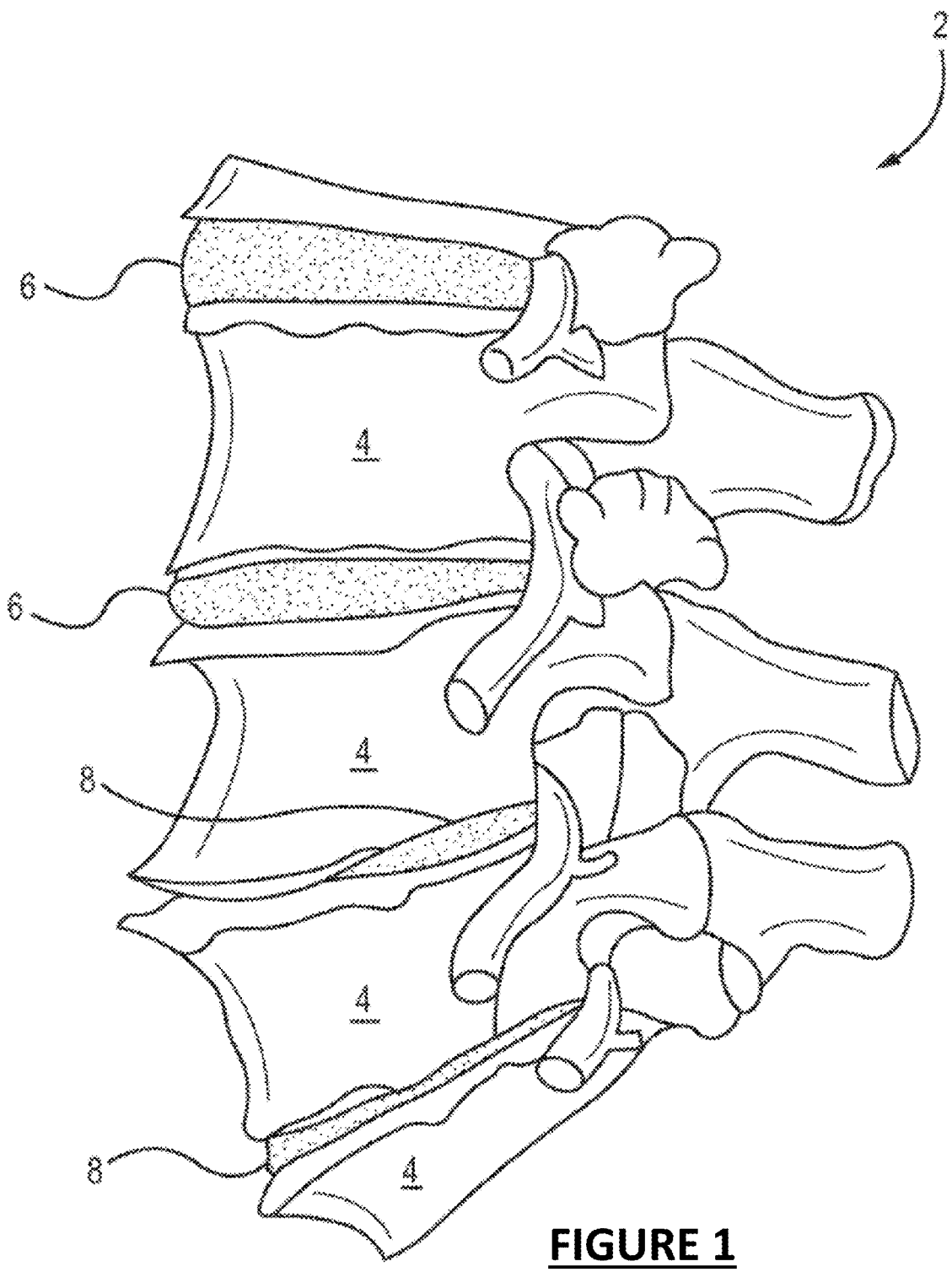
FIG. 1 depicts a portion of a patient's spinal column.

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

Various embodiments of surgical tools and trailing devices described herein may have particular utility in combination with implants and/or system components disclosed in co-pending U.S. patent application Ser. No. 15/244,868 entitled "INTERVERTEBRAL IMPLANTS AND RELATED SYSTEMS AND METHODS," filed Dec. 1, 2015, the disclosure of which is incorporated by reference herein in its entirety.

FIG. 1 shows a portion of a patient's spinal column 2, including vertebra 4 and intervertebral discs 6. As noted earlier, each disc 6 forms a fibrocartilaginous joint between adjacent vertebrae 4 so as to allow relative movement between adjacent vertebrae 4. Beyond enabling relative motion between adjacent vertebrae 4, each disc 6 acts as a shock absorber for the spinal column 2. Each disc 6 comprises a fibrous exterior surrounding an inner gel-like center which cooperate to distribute pressure evenly across each disc 6, thereby preventing the development of stress concentrations that might otherwise damage and/or impair vertebrae 4 of spinal column 2. Discs 6 are, however, subject to various injuries and/or disorders which may interfere with a disc's ability to adequately distribute pressure and protect vertebrae 4. For example, disc herniation, degeneration, and infection of discs 6 may result in insufficient disc thickness and/or support to absorb and/or distribute forces imparted to spinal column 2. Disc degeneration, for example, may result when the inner gel-like center begins to dehydrate, which may result in a degenerated disc 8 having decreased thickness. This decreased thickness may limit the ability of degenerated disc 8 to absorb shock which, if left untreated, may result in pain and/or vertebral injury.

The present disclosure includes examples that relate to, among other things, intradiscal, extradiscal, or interdiscal implants. The interbody devices and systems (including, cages and/or plate devices) disclosed herein may be used as, for example, but not limited to, standalone devices, anterior lumbar interbody fusion devices, standalone anterior low-profile plating devices, an interlocking of standalone devices to create hybrid devices, modular systems to allow interchangeability, and the like. Each of the examples disclosed herein may include one or more features described in connection with any of the other disclosed examples.

According to an aspect of the disclosure, surgical tools for preparing an anatomical site for implanting an interbody system are disclosed. The interbody system comprises a cage having a cage body that optionally includes a graft chamber having a volume that receives graft material, a first sagittal wall having an inner wall surface that forms a first sagittal portion of the graft chamber, a second sagittal wall having an inner wall surface that forms a second sagittal portion of the graft chamber, an aft-wall having an inner wall surface that forms a posterior coronal portion of the graft chamber, and a wall or wall membrane that forms an anterior coronal portion of the graft chamber. The interbody system may further comprise an interbody device that includes an aperture that receives a bone fastener, wherein the wall or wall membrane interacts with the bone fastener. In various embodiments, the interbody device may comprise two or more apertures that receive two or more respective bone screws.

In various embodiments, the surgical tools disclosed herein can include a multi-function tool which functions as a surgical trial and a tool guide. Once positioned in a desired location and/or orientation of the patient anatomy, the multi-function tool will desirably guide a multi-axial reaming tool in preparing the underlying spinal anatomy (including bony and/or softer tissues) to receive a surgical implant and related anchoring devices such as bone screws.

Figure 2A:
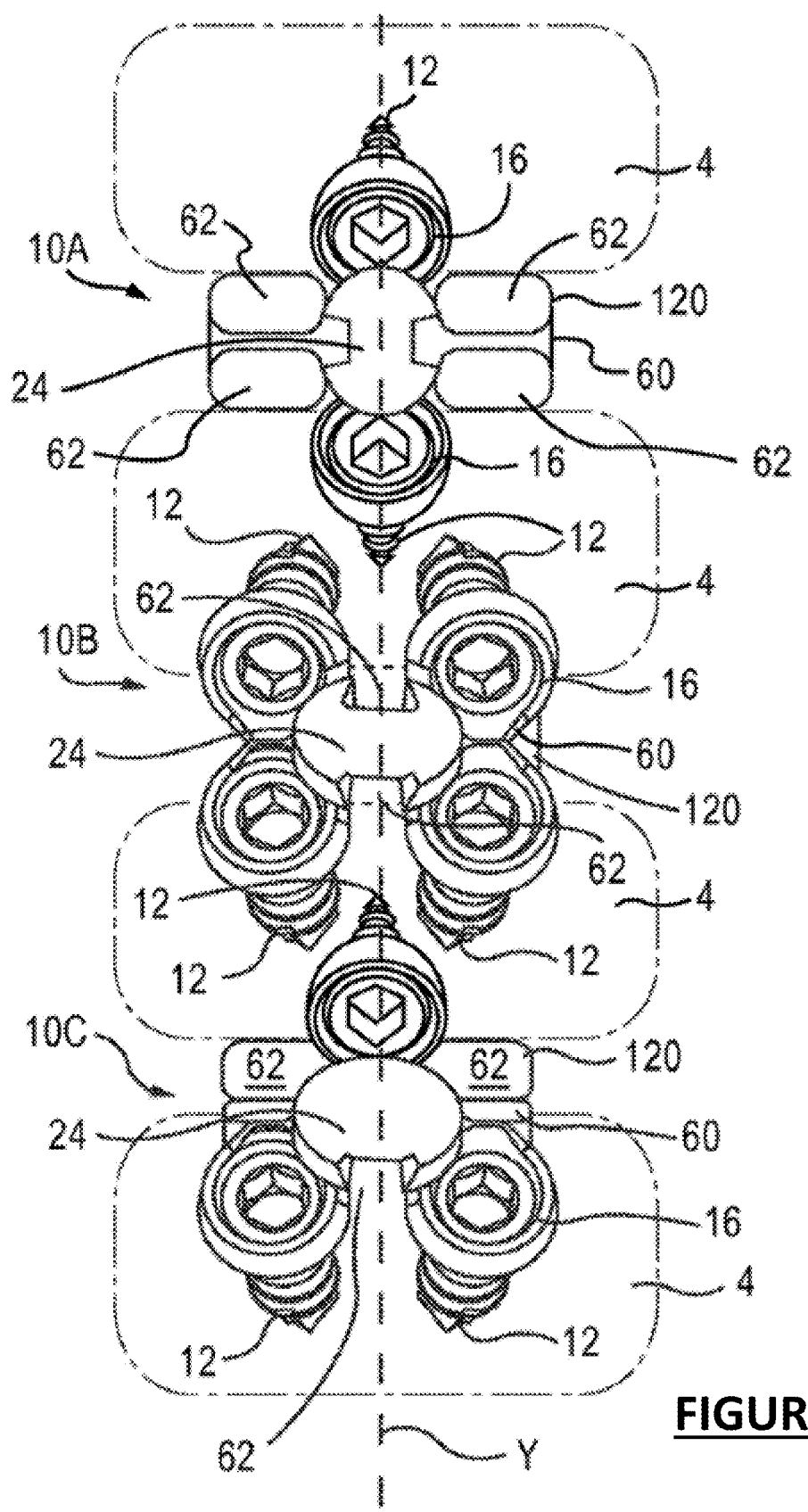
FIG. 2A depicts one exemplary embodiment of stacked interbody devices.

FIG. 2A illustrates a spinal column 2 having a plurality of interbody devices 10A, 10B and 10C disposed between vertebrae 4 (shown in phantom lines). As shown, each of the plurality of interbody devices 10A, 10B, 10C may be arranged along a central longitudinal axis (e.g., axis Y of FIG. 2) within a common plane. That is, one or more of the screws 12 extending through one or more of the interbody devices 10 may be positioned along the central longitudinal axis Y in a common plane (e.g., screws 12 through a first interbody device 10A of FIG. 2A, for example, positioned so as to be aligned along axis Y). Additionally or alternatively, one or more screws 12 extending through one or more of the interbody device 10 may be positioned on a common plane and spaced (either equidistantly or nonequidistantly) from a central longitudinal axis Y (e.g., screws 12 through second interbody device 10B of FIG. 2A). Additionally or alternatively, one or more of the screws 12 extending through one or more of the interbody devices 10 may be positioned such that some are positioned along the central longitudinal axis Y while others are spaced (either equidistantly or nonequidistantly) from the central longitudinal axis Y along a common plane (e.g., screws 12 through second interbody device 10C of FIG. 2A).

Figure 2B:
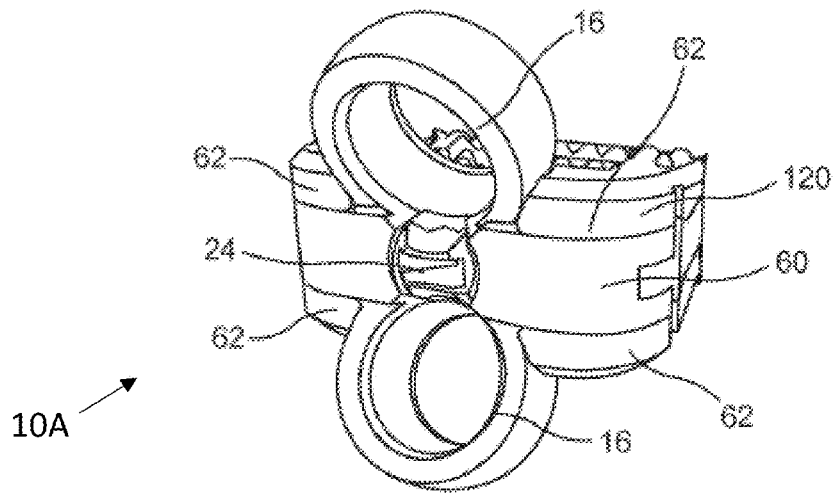
FIG. 2B depicts a perspective view of an interbody device incorporating a pair of anchor screws.

For example, a first interbody device 10A may be disposed between adjacent vertebrae 4. A perspective view of the first interbody device 10A, without screws 12, is shown in FIG. 2B. As shown in FIG. 2A, the first interbody device 10A may be configured to receive two screws 12. As such, the first interbody device 10A may include a frame 60 that includes one or more apertures 16 and optionally an offsetting element 24 therebetween. The frame 60 may define one or more windows 62 along a coronal plane of first interbody device 10A. Accordingly, in the coronal view of first interbody device 10A placed between two adjacent vertebrae 4 under X-ray vision, as shown in FIG. 2A, windows 62 remain radiolucent such that fusion within and/or through window 62 may be observed. Optionally, the first interbody device 10A may include a graft containment sheath 120. Graft containment sheath 120 may be disposed along one or more portions of frame 60. For example, a graft containment sheath 120 may be wrapped around frame 60 and may substantially fill or encompass windows 62 of frame 60. That is, a graft containment sheath 120 may be configured so as to cooperate with the frame 60 of the first interbody device 10A such that bone graft material 70 may be retained within desired portions of first interbody device 10A so as to facilitate fusion.

Figure 2C:
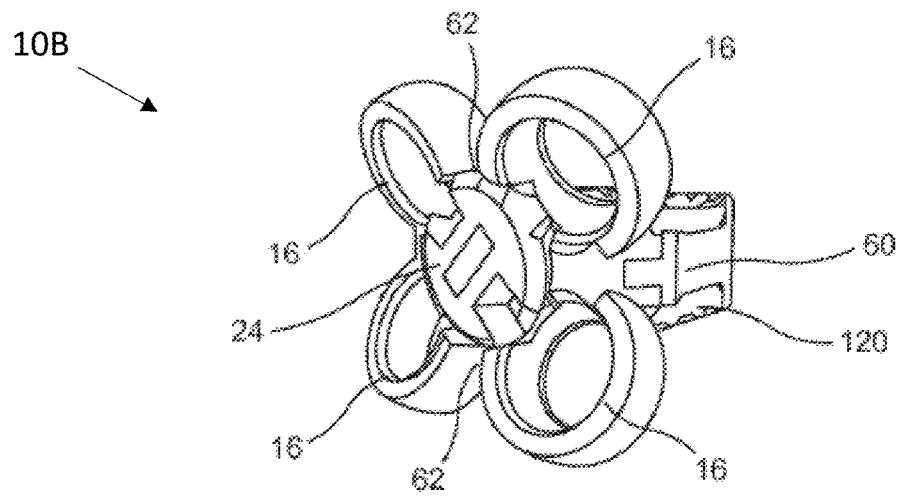
FIG. 2C depicts a perspective view of an interbody device incorporating four anchor screws.

Further, as shown in FIG. 2A, a second interbody device 10B may be disposed between adjacent vertebrae 4. A perspective view of the second interbody device 10B, without screws 12, is shown in FIG. 2C. As shown in FIG. 2A, the second interbody device 10B may be configured to receive four screws 12. As such, the second interbody device 10B may include a frame 60 with one or more apertures 16 and an offsetting element 24 therebetween. The frame 60 may define one or more windows 62 along a coronal plane of the second interbody device 10B. Accordingly, in the coronal view of the second interbody device 10B placed between two adjacent vertebrae 4 under X-ray vision, as shown in FIG. 2A, windows 62 may remain radiolucent such that fusion within and/or through window 62 may be observed. Optionally, the second interbody device 10B may include a graft containment sheath 120. The graft containment sheath 120 may be disposed along one or more portions of frame 60. For example, a graft containment sheath 120 may be wrapped around frame 60 and may substantially fill or encompass windows 62 of frame 60. That is, the graft containment sheath 120 may be configured so as to cooperate with frame 60 of second interbody device 10B such that bone graft material 70 may be disposed along desired portions of the second interbody device 10B so as to facilitate fusion.

Figure 2D:
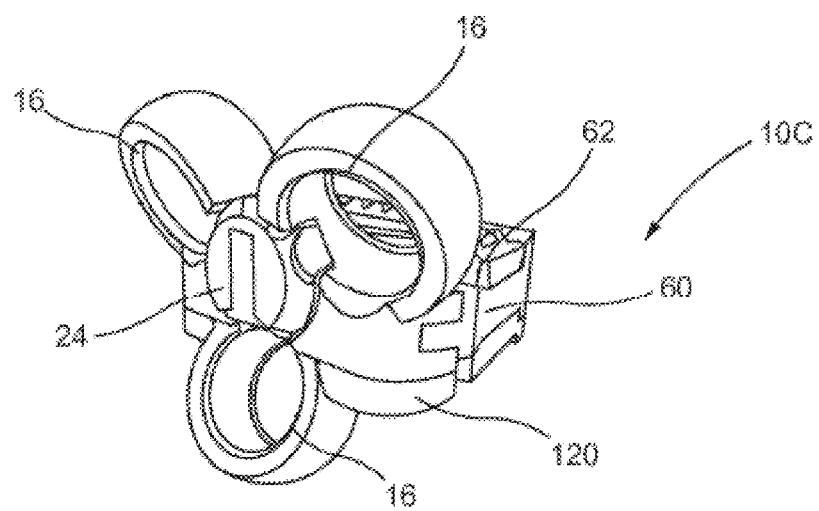
FIG. 2D depicts a perspective view of an interbody device incorporating three anchor screws.

Additionally, as shown in FIG. 2A a third interbody device 10C may be disposed between adjacent vertebra 4. A perspective view of the third interbody device 10C, without screws 12, is shown in FIG. 2D, which may be configured to receive three screws 12. As such, the third interbody device 10C may include a frame 60 with one or more apertures 16 and an offsetting or locking element 24 therebetween. The frame 60 may define one or more windows 62 along a coronal plane of third interbody device 10C. Accordingly, in the coronal view of the third interbody device 10C placed between two adjacent vertebrae 4 under X-ray vision, as shown in FIG. 2A, windows 62 remain radiolucent such that fusion within and/or through window 62 may be observed. Optionally, the third interbody device 10C may include a graft containment sheath 120, which may be disposed along one or more portions of frame 60. For example, a graft containment sheath 120 may be wrapped around the frame 60 and may substantially fill or encompass windows 62 of frame 60. That is, a graft containment sheath 120 may be configured so as to cooperate with frame 60 of third interbody device 10C such that bone graft material 70 may be retained within desired portions of third interbody device 10C so as to facilitate fusion.

Figure 3A:
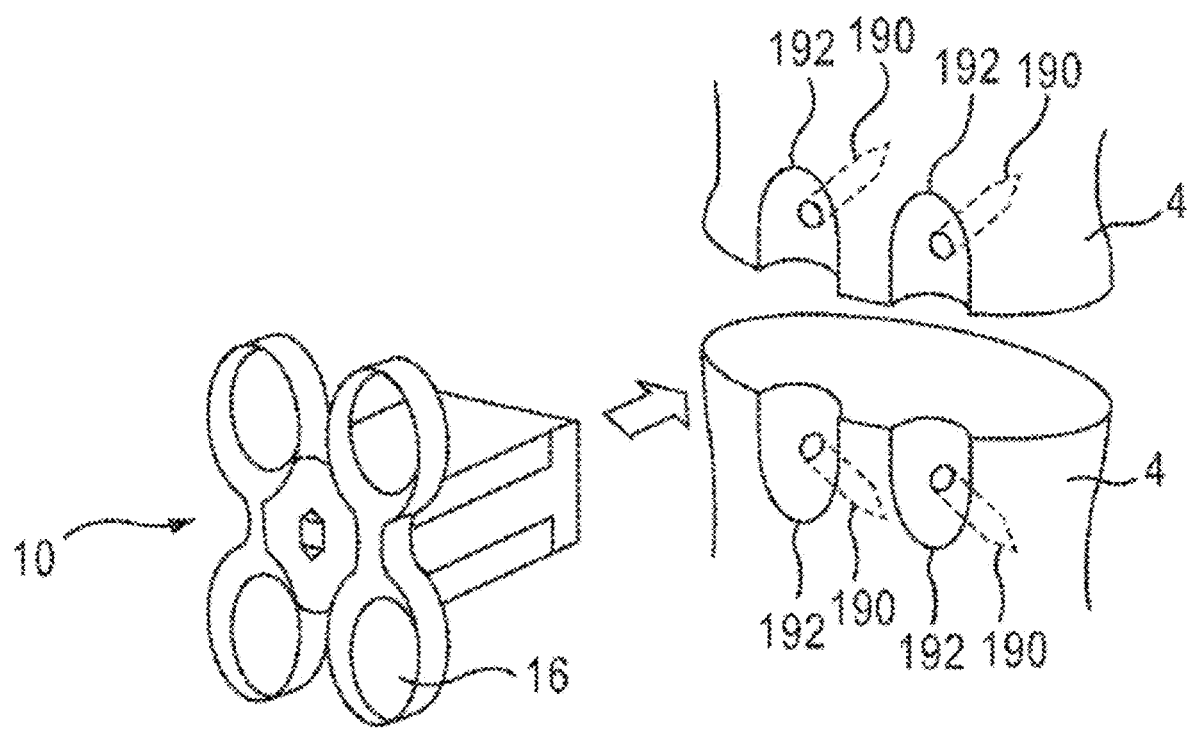
FIG. 3A depicts an interbody device being advanced into a prepared anatomical space between adjacent vertebra.
Figure 3B:
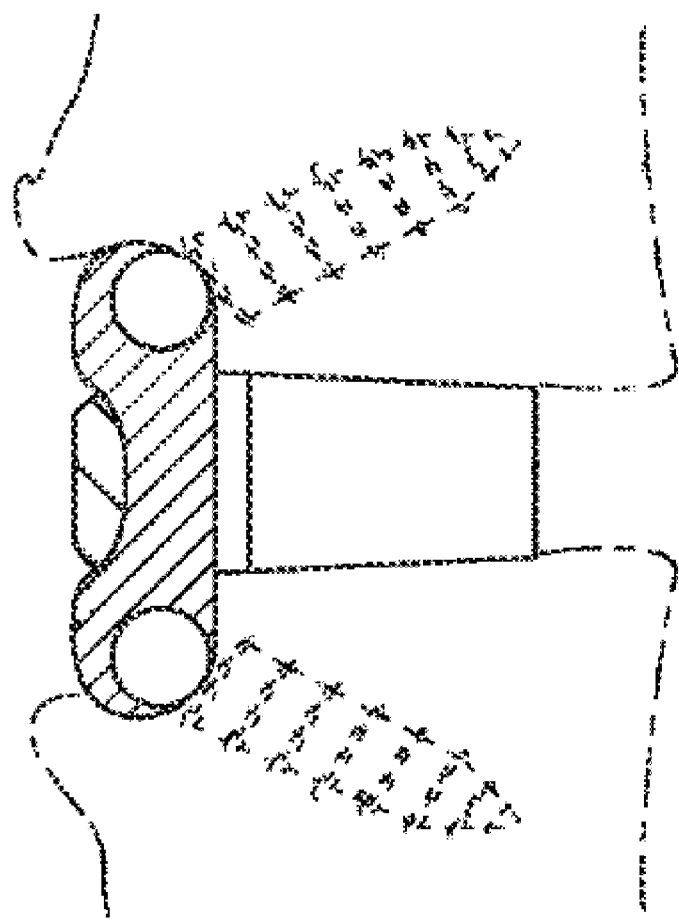
FIG. 3B depicts a side view of the interbody device of FIG. 3A, when implanted between the adjacent vertebra.

As shown in FIGS. 2A and 3B, a screw 12 can extend through the first interbody device 10A towards the second interbody device 10B and into vertebra 4, and screws 12 can extend through the second interbody device 10B toward the first interbody device 10A and into the same vertebra 4m, with these screws spaced from one another. That is, screws 12 may be arranged and/or oriented so as not to interfere with one another as each passes through a respective interbody device 10 and into vertebra 4. Indeed, screw 12 extending through first interbody device 10 and into vertebra 4 may be received within vertebra 4 between screws 12 extending through second interbody device 10B and into vertebra 4. Likewise, screws 12 extending through second interbody device 10B toward third interbody device 10C and into vertebra 4, and screws 12 extending through the third interbody device 10C toward second interbody device 10B and into the same vertebra 4 may be spaced from one another. Accordingly, the first interbody device 10A, the second interbody device 10B, and the third interbody device 10C may be stacked along spinal column 2 without interfering with one another. In such a manner, multiple portions of a spinal column 2 may be treated simultaneously.

It should be understood that each of the first interbody device 10A, the second interbody device 10B, and/or the third interbody device 10C could potentially be utilized alone for treatment of a single spinal level, as well as utilized in various combinations and/or in complimentary or inverted orientations, depending upon surgical need and the patient's particular anatomy. The stacking of these devices in FIG. 2A is merely representative, and any arrangement of interbody devices 10 may be utilized and/or stacked along a given spinal column 2. Accordingly, any appropriate arrangement of any of the above disclosed interbody devices 10 may be arranged along spinal column 2 so as to produce any desired therapeutic effect.

During a procedure for any of ACIF, ALIF, DLIF, PLIF, and/or TLIF, a multi-function tool (MF tool), guide or milling body can be employed, with various embodiments of this tool functioning as a surgical trial and a tool guide for preparing the spinal anatomy for an implant. If desired, MF tools of various trialing and/or distraction sizes may be utilized, with a portion of the MF tool forcibly inserted between adjacent vertebrae 4 so as to determine an appropriate size and/or positioning of an interbody device 10 to be received within the spinal column 2.

As shown in FIG. 4, an exemplary tool 200 may include a shaft 215 coupled to a body 220 for manipulation thereof. That is, the shaft 215 may be any appropriate structure coupled to the body 220 and having sufficient columnar strength to facilitate insertion and retraction of an insertion trial 225 between two adjacent vertebrae 4. In some arrangements, the shaft 215 may be removably coupled to the body 220. If desired, the insertion trial 225 may include a reduced profile leading edge portion (not shown) for insertion between adjacent vertebral bodies. For example, the insertion trial 225 may include a tapered nose 227, if desired, which may assist a medical professional to insert and/or retract the trial 225 between adjacent vertebrae 4. The body 220 and/or shaft 215 may comprise any one or more (or various combinations thereof) of metal, plastic, ceramic and/or elastomers, and in some embodiments the insertion trial 225 and/or body 220 may be configured for selective expansion, allowing a single MF tool to assume varying trial heights.

In one exemplary embodiment, the shaft 215 may be removably coupled to the body 220. For example, a distal end of the shaft 215 may be threaded so as to cooperate with a threaded hole (not shown) in the body 220, or vice versa. In some arrangements, the shaft 215 may form a portion of a kit including a shaft 215 and a plurality of bodies 220 and/or insertion trials 225. Each body and/or insertion trial may have varied dimensions (e.g., length, width, height, etc.), with a modular connection allowing a variety of insertions trials of differing sizes to be utilized with each individual body 220. Accordingly, a medical professional may selectively choose one or more components on the kit to couple together to create a desired MF tool. It should be understood that any appropriate coupling structure other than threading is also contemplated. For example, any corresponding mating arrangement may be used to selectively couple and decouple the shaft 215 from body 220, and so on.

Figure 4A:
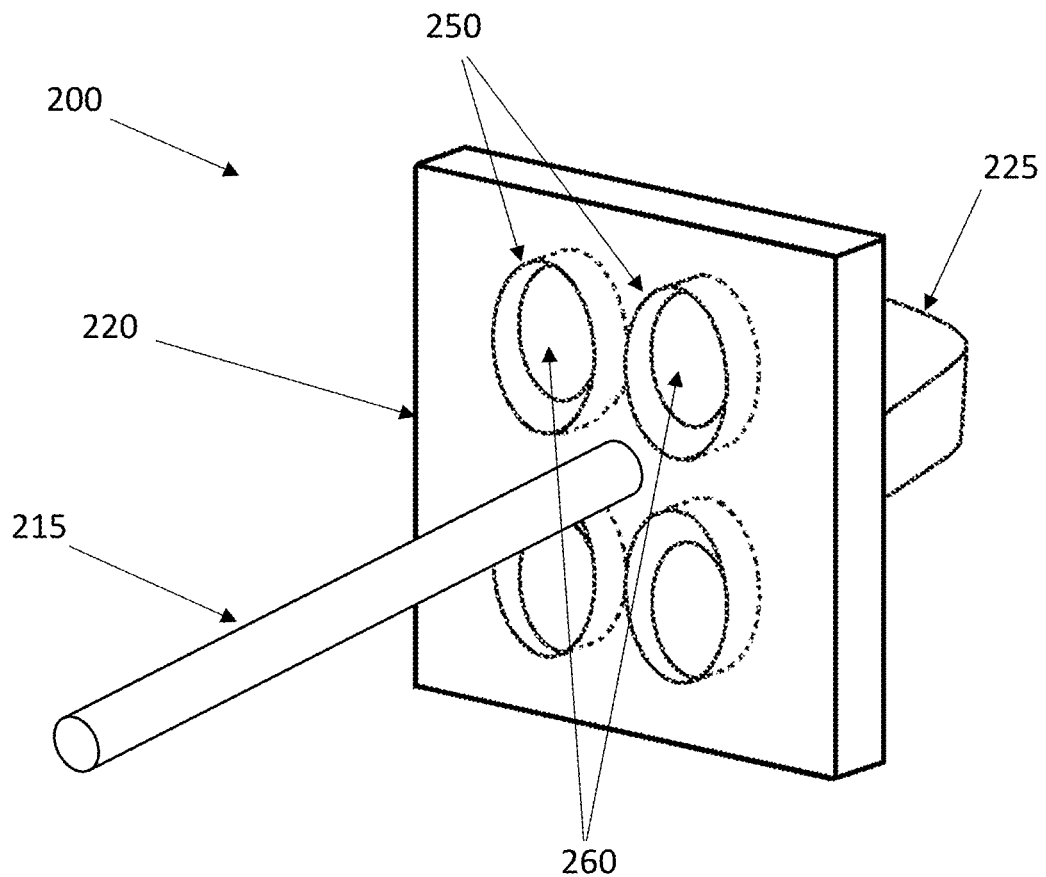
FIG. 4A depicts a perspective view of one exemplary embodiment of a multi-function tool.

Upon insertion of the MF tool with the insertion trial 225 positioned between the adjacent vertebral bodies, the adjacent vertebrae may be spread apart from one another to a desired degree, and one or more tools may be utilized to prepare the vertebrae for insertion of a final implant device. As best seen in FIG. 4A, the MF tool 200 can also include one or more openings 250 which can desirably acts as positioning, alignment and/or depth guides that allow a multi-axial reaming tool to be used to prepare the vertebrae, such as the reaming tool shown in FIGS. 6A and 6B. Desirably, the MF tool will include a number and/or positioning of bore holes 260 that correspond to the anchoring holes of the intended implant device, such as two bore holes for the implant of FIG. 2B, four bore holes for the implant of FIG. 2C, and three bore holes for the implant of FIG. 2D.

Figure 4B:
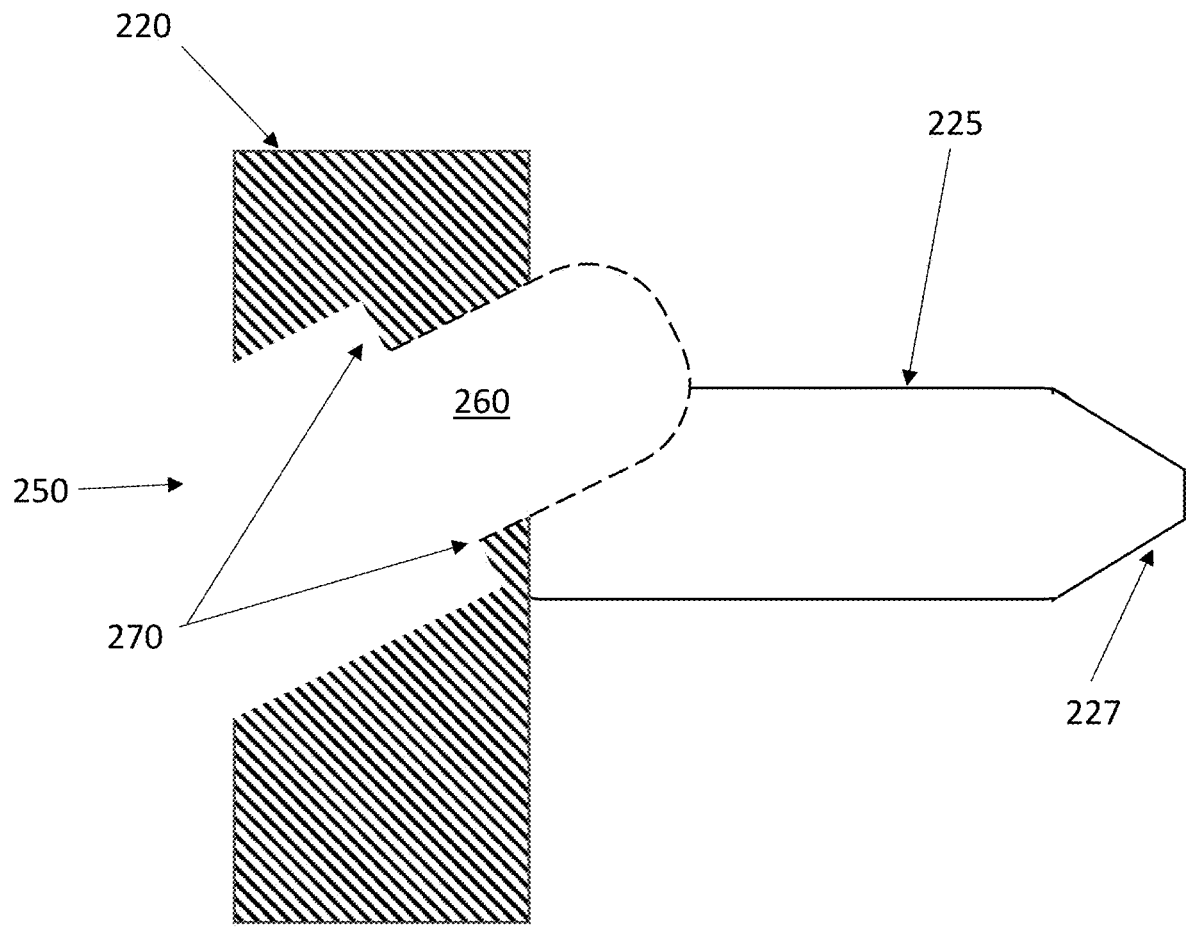
FIG. 4B depicts a cross-sectional side view of the multi-function tool of FIG. 4A.

FIG. 4B depicts a cross-sectional view of a single upper alignment hole of the MF tool of FIG. 4A, wherein the opening 250 can be seen extending into the body 220, with a smaller diameter bore hole 260 extending out a back portion of the body 220 towards the insertion trial 225. In this embodiment, a shoulder 270 is disposed at the bottom of the opening 250 and at the top of the bore hole 260, and this shoulder 270 can desirably provide a depth stop or similar guiding surface for the reaming tool of FIGS. 6A and 6B.

Figure 5A:
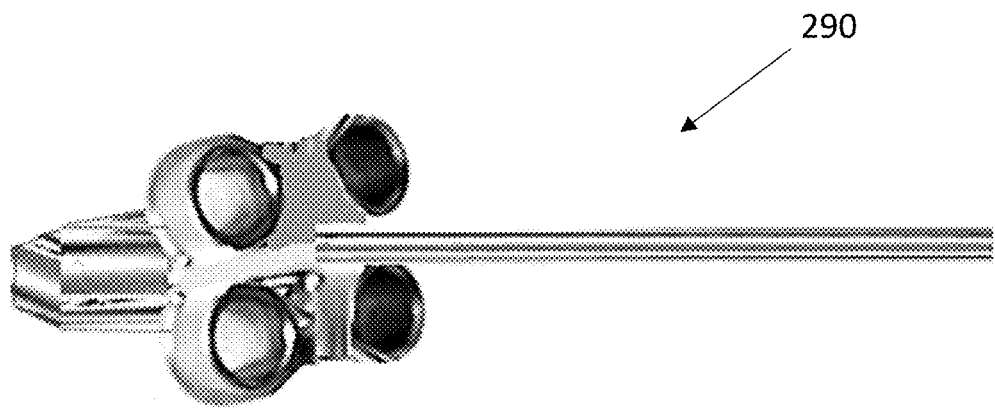
FIG. 5A depicts a perspective view of another exemplary embodiment of a multi-function tool.
Figure 5B:
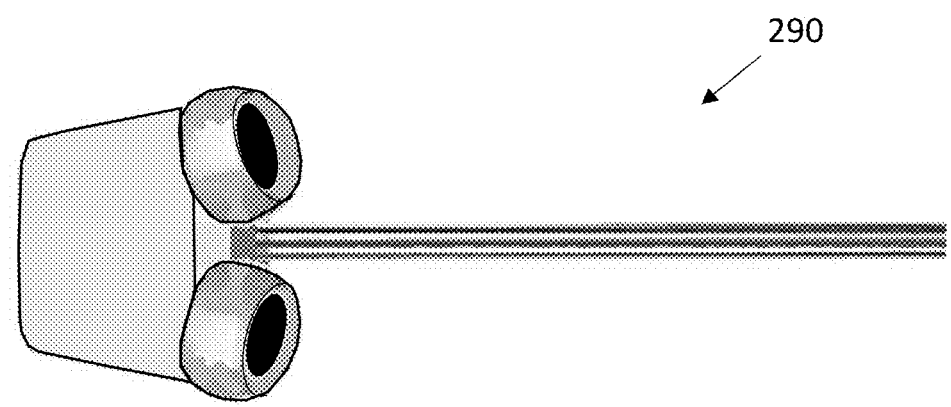
FIG. 5B depicts a top plan view of the multi-function tool of FIG. 5A.

FIGS. 5A and 5B depict views of an alternative embodiment of a MF tool 290, which can desirably function as (1) an intervertebral trial sizing device, (2) an anchoring hole trajectory guide for positioning and/or guiding the drilling direction of anchor holes in bones and/or other tissue removal (i.e., tap and drill device), and/or (3) a positive stop device for guiding drilling and/or reaming depth. In various embodiments, the a surgical procedure for utilizing such a device can include (1) selecting a proper footprint and trial size of a MF tool, (2) insert intervertebral trial and place MF tool in desired location on patient anatomy, (3 (operate awl/drill and/or tapping devices to prepare relevant anatomy, (4) remove MF tool and insert selected implant, and (5) insert screws or other anchoring devices and secure implant to target anatomy.

FIGS. 6A and 6B depict various views of one embodiment of a multi-axial reaming tool 300 for use in preparing the vertebral bodies for insertion of an interbody device. The multi-axial reaming tool 300 can include a shaft 310, a multi-axial or universal joint 320 or similar flexible section or section (i.e., a hinge gear), a cylindrical guide 330 having an engagement or shoulder section 340, a bone drill or reamer 350 and a guidance or pilot hole feature 360, such as an awl tip, a drill tip or a tap.

In use, a distal end of the reaming tool 300 can desirably be advanced into an opening 250 of the MF tool, with the outer walls of the cylindrical guide 330 sliding within and aligned by the inner walls of the opening 250 and the reamer 350 passing into and through bore hole 260. As the reaming tool 300 is advanced further into opening 250 (with the reamer is being rotated and/or otherwise operated), the reamer 350 will desirably be cutting and/or removing various tissues with which it comes into contact. Once the reaming tool 300 has been fully advanced into the opening 250, the shoulder section 340 of the reaming tool 300 will desirably come into contact with the shoulder 270 at the bottom of the opening 250, which desirably prevents further unwanted advancement of the reaming tool 300. The reaming tool 300 can then be removed from the MF tool and utilized in a similar fashion in the remaining openings of the MF tool.

Desirably, the reaming tool 300 will be utilized to form one or more holes and/or counter bores within the targeted vertebra in a desired alignment and/or depth for receipt of suitable fasteners such as, for example, screws. In addition, the reaming surfaces may be useful in removing various intervening anatomy which could interfere with optimal placement of the implant and/or anchoring screws, including anatomical features that might be difficult for a surgeon to directly visualize during the surgical procedure. As best depicted in FIG. 3A, each vertebra 4 may include one or more pilot holes 190 formed by the pilot hole feature 360 of the MF tool, and one or more counter bores 192 formed by the reamer 350 of the tool.

As shown, in FIG. 3A, for example, two pilot holes 190 and two counterbores 192 may be formed in each vertebra 4, which will desirably prepare the adjacent vertebrae to receive an interbody device 10 therebetween. Once the desired pilot holes 190 and/or counterbores 192 have been formed, the reaming tool and MF tool may be removed, and an interbody device which corresponds to the MF tool may be inserted between adjacent vertebra 4 and secured using screws or other anchoring devices inserted through one or more apertures of the interbody device and into the counterbore and/or pilot hole so as to secure the interbody device in place as shown in FIGS. 2A and 3B.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Various embodiments described herein include the design and manufacturing of a variety of implants, trial implants and related surgical tools, which may include devices having various pre-defined shapes, sizes, widths, spans, thicknesses and/or contours based, at least partially, off of anatomical shape information obtained from one or more pre-operative scans (i.e., x-ray, sonogram, CT scan, MRI, etc.) of the patient's anatomy. Various embodiments described herein can be used as individual surgical tools to prepare various tissue structures to receive an implant, as well as to protect adjacent tissue structures from cutting tools, and some embodiments may include patient specific features, such as patient specific cutting guides and/or cutting tools.

Various embodiments described herein can be used in conjunction with patient specific implants that may have been constructed specifically for an individual patient, including MF tools where some portions and/or contours of the tool may be constructed in a reverse mold of the patient's bony and/or other tissue surfaces. The shape of such tools can be determined from scans or digital images like a CT Scan or MRI scan. In many cases, such tools may help the surgeon determine an ideal position for cutting and/or preparing anatomical structures for receiving implant components, such as spinal arthroplasty components.

All references, including publications, patent applications and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. AH methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reaming at least one cavity in a vertebral body, the method comprising: resecting a posterior portion of the vertebral body which is to be reamed thereby forming a resected surface; locating a reamer guide having at least one reamer opening at least partially on the resected surface, the reamer guide including an insertion trial portion extending distally from the reamer guide and at least partially into an intervertebral space adjacent to the vertebral body; inserting a reamer into the at least one reamer opening of the reamer guide, the reamer including a multi-axial rotation element located between a reamer head and a reamer driving mechanism; reaming the vertebrae through the at least one reamer opening; and removing the reamer and reamer guide from the vertebral body.

2. The method of claim 1, wherein the at least one opening includes a inwardly extending shoulder which reduces a diameter of the at least one opening.

3. The method of claim 1, wherein the reamer guide includes an elongated shaft coupled to a body at a distal end, the body having at least one tubular opening extending therethrough, the tubular opening having a first internal diameter section and a second internal diameter section, the first internal diameter section being larger in diameter than the second internal diameter section, the first internal diameter section separated from the second internal diameter section by a shoulder section having a shoulder face positioned towards the elongated shaft.

4. The method of claim 3, wherein the body further includes an insertion trial portion extending distally from the body, the insertion trial portion having a tapered distal tip.

5. The method of claim 3, wherein the elongated shaft is removably coupled to the body.

6. The method of claim 4, wherein the insertion trial portion is removably coupled to the body.

7. The method of claim 1, wherein the insertion trial portion is configured for selective expansion.

8. The method of claim 1, wherein the insertion trial portion includes a removably coupled shaft.

9. The method of claim 1, wherein the at least one reamer opening corresponds to one or more anchoring holes formed in the vertebral body for an implant device.

10. The method of claim 1, wherein the multi-axial rotation element comprises a flexible section.

11. The method of claim 1, wherein the multi-axial rotation element comprises a hinge gear.

12. The method of claim 1, wherein the multi-axial rotation element comprises a multi-axial joint.

13. The method of claim 1, wherein the multi-axial rotation element comprises a universal joint.

14. The method of claim 1, wherein the reamer further comprises a cylindrical reamer guide.

15. The method of claim 14, wherein the multi-axial rotation element is positioned between a proximal end of the reamer and the cylindrical reamer guide.

16. The method of claim 2, wherein the step of reaming the vertebrae through the at least one reamer opening comprises advancing the reamer into the at least one reamer opening of the reamer guide until a cylindrical reamer guide on the reamer contacts the inwardly extending shoulder.

17. The method of claim 1, wherein a distal end of the reamer includes an awl tip.

18. The method of claim 1, wherein a distal end of the reamer includes a drill tap.

19. The method of claim 1, wherein a distal end of the reamer includes a tap.

20. The method of claim 1, further comprising the step of forming a pilot hole in the vertebral body.

* * * * *